United States Patent [19]

Ganci

[11] Patent Number: 5,502,192
[45] Date of Patent: Mar. 26, 1996

[54] PROCESS FOR THE PREPARATION OF QUINACRIDONES FROM DIHYDROQUINACRIDONES IN AN AQUEOUS MEDIUM

[75] Inventor: James B. Ganci, Wilmington, Del.

[73] Assignee: Ciba-Geigy Corporation, Tarrytown, N.Y.

[21] Appl. No.: 287,348

[22] Filed: Aug. 8, 1994

[51] Int. Cl.$^6$ .................................................. C09B 48/00
[52] U.S. Cl. ............................................. 546/49; 546/56
[58] Field of Search ................................... 546/49, 56

[56] References Cited

U.S. PATENT DOCUMENTS

| | | | |
|---|---|---|---|
| 2,821,529 | 1/1958 | Struve | 546/56 |
| 3,024,239 | 3/1962 | Calieze | 546/49 |
| 3,148,075 | 8/1964 | Ehrich | 546/49 |
| 3,475,436 | 10/1967 | Cooper et al. | 546/49 |
| 3,532,867 | 11/1967 | Adachi | 546/49 |
| 3,632,588 | 1/1972 | Ehrich | 546/49 |
| 3,738,988 | 6/1973 | Jackson et al. | 546/49 |
| 4,812,568 | 3/1989 | Herzog et al. | 546/49 |
| 5,093,497 | 3/1992 | Schutze et al. | 546/56 |
| 5,281,269 | 1/1994 | Ganci et al. | 546/49 |
| 5,286,863 | 2/1994 | Bäbler | 546/49 |

FOREIGN PATENT DOCUMENTS

| | | |
|---|---|---|
| 1225352 | of 1960 | France . |
| 1328160 | 4/1963 | France . |
| 1210110 | 2/1966 | Germany . |
| 53-94334 | 8/1978 | Japan . |
| 887373 | 1/1962 | United Kingdom ............ 546/49 |
| 94-10249 | 5/1994 | WIPO ............................ 546/56 |

OTHER PUBLICATIONS

Derwent Abstr 67912A/38 of JP 5394334 (1978).
S. Sabana et al Chemical Reviews vol. 67 No. 1, pp. 1–18 (1967).
Derw. Abst. 16435T of JP 47–7703 (1972).
Derw. Abst. 77–85331Y/48 of JP 83040589 (1977).

*Primary Examiner*—Donald G. Daus
*Attorney, Agent, or Firm*—George R. Dohmann

[57] ABSTRACT

An aqueous phase air oxidation process for the for the preparation of unsubstituted and substituted quinacfidone pigments is disclosed. The process involves an oxidation step wherein a 6,13-dihydroquinacridone is convened to the corresponding quinacfidone, utilizing a quinone compound and molecular oxygen as oxidizing agent, in a basic, aqueous reaction medium, in the presence of a nonionic, polar organic material which forms a second liquid phase in the basic reaction medium and which is present in a minor amount relative to the amount of aqueous base in the reaction medium. The quinacridones prepared by this process are useful as pigments.

27 Claims, No Drawings

1

PROCESS FOR THE PREPARATION OF QUINACRIDONES FROM DIHYDROQUINACRIDONES IN AN AQUEOUS MEDIUM

SUMMARY

Disclosed is a process for oxidizing a dihydroquinacridone to a quinacridone utilizing a quinone compound and molecular oxygen as the oxidizing agent, in a basic, aqueous reaction medium, in the presence of a minor amount of a polar, nonionic, organic material which forms a liquid, organic second-phase under the reaction conditions.

BACKGROUND

Quinacridone pigments are well known in the art and can be prepared by a number of processes some of which involve oxidizing an unsubstituted or substituted 6,13-dihydroquinacridone to the correspondingly substituted quinacridone.

For example, U.S. Pat. No. 2,821,529 describes a process wherein various 6,13-dihydroquinacridones are oxidized to the corresponding quinacridone by heating a mixture containing the dihydroquinacridone and a mild oxidizing agent in an alkaline reaction medium. The medium is a mixture containing a major portion of an organic solvent, generally an alcohol, and a minor amount of water. The amount of water present in the reaction medium is small relative to the amount of the organic solvent.

The literature also describes processes for oxidizing a dihydroquinacridone to the corresponding quinacridone by utilizing molecular oxygen and a quinone compound as the oxidizing agent. Such a reaction is often referred to as an "air oxidation" because air is a preferred source of the molecular oxygen. In general, such oxidation processes are disclosed as taking place in an alkaline medium, usually an organic solvent containing a minor amount of water, in the presence of a quinone compound and molecular oxygen. The molecular oxygen is introduced to the reaction medium by bubbling an oxygen containing gas through the reaction medium or by blowing the oxygen containing gas above the surface thereof. Although the literature describes the quinone compound both as a catalyst and as an oxidizing agent, U.S. Pat. No 3,024,239 discloses that the quinone is an oxidizing agent which is reduced to the corresponding leuco compound during the oxidation of the dihydroquinacridone. The molecular oxygen regenerates the quinone so that less than the stoichiometric amount of the quinone is required for the reaction to proceed to completion.

U.S. Pat. No. 3,475,436 discloses an air oxidation process wherein the reaction medium contains a major portion of tetramethylene sulfone and a relatively small amount of water. Similar processes which utilize an alkaline medium containing a major portion of other organic solvents, such as dimethyl sulfoxide, dimethylacetamide, alkanediols, $C_1$–$C_3$ alcohols caprolactam and N-alkyl-2-pyrrolidone, usually in the presence of a relatively small amount of water, are also known in the art.

It is also known to perform the air oxidation of dihydroquinacridones in an aqueous reaction medium. However, the known aqueous processes are carried out in the presence of a divalent metal ion or a quaternary ammonium salt. For example, U.S. Pat. No. 3,738,988 discloses a process wherein an aqueous medium is utilized. However, U.S. Pat. No. 3,738,988 discloses that the oxidation step should be carried out in the presence of divalent iron, cobalt or nickel ions in order to increase the effectiveness of the oxidation.

U.S. Pat. No. 5,093,497 requires the presence of a quaternary ammonium salt in order to overcome disadvantages in known air oxidation processes in both an aqueous reaction medium or an organic reaction medium. The present invention is based on the discovery that excellent conversion of the 6,13-dihydroquinacridone to the corresponding quinacridone is achieved in an aqueous medium via an air oxidation process if the aqueous reaction medium also contains a relatively minor amount of a nonionic, polar organic material which forms a liquid, organic second-phase in the reaction mixture. The present process provides high yields of quinacridones having superior purity compared to the product of known aqueous air oxidation processes. An additional advantage of the disclosed process is that it is not necessary to perform the oxidation in the presence of a surfactant in order to obtain a reasonable yield of high purity product. In addition, the present process eliminates the need for uneconomical quaternary ammonium compounds and metal salts, along with any potential disposal problems associated with the presence of such additives.

DETAILED DESCRIPTION

In general, the present invention relates to a process for oxidizing an unsubstituted or substituted dihydroquinacridone to the corresponding quinacridone in a basic, aqueous reaction medium, in the presence of a relatively minor amount of a nonionic, polar organic material which forms a second liquid phase in the basic reaction medium, utilizing a quinone compound and molecular oxygen as oxidizing agent. Preferably, the reaction medium comprises, per 100 parts by weight of aqueous base, from 6 to 12 parts by weight of the 6,13-dihydroquinacridone and from 0.5 to 3 parts by weight of the organic material. In particular, the reaction medium comprises from 7.5 to 10 parts by weight of the 6,13-dihydroquinacridone and 0.5 to 1.2 parts by weight of the organic material.

The expression "aqueous base" is used in this application to refer to the combined weights of the base and water in the aqueous reaction medium.

The presence of larger amounts of the second-phase forming organic material also produces the desired product at efficient yields. However, these larger amounts do not have any practical advantage.

In general, the nonionic, polar organic material is any organic compound which contains at least one polar functional group, is nonionic, and which forms a liquid, organic second-phase in the highly caustic reaction medium. Examples of suitable nonionic, polar functional groups include hydroxy, oxy (—O—) and amino. The organic material also includes mixtures of such compounds that form a liquid, organic second-phase in the reaction medium.

It is essential for the organic material to form a liquid second-phase in the highly caustic reaction medium. However, the organic material should also be at least slightly soluble in pure water and can be up to completely miscible with pure water. In addition, the organic material should be relatively unreactive and should not adversely interfere with the oxidation reaction.

It is possible that the oxidation occurs in the organic second-phase or at the interface between the organic and aqueous phases. The nonionic, polar organic material may also facilitate the oxidation by lowering the viscosity of the aqueous slurry. Most likely, a combination of factors contribute to the facilitation of the oxidation. Therefore, any discussion of the mechanism by which the organic material facilitates the reaction is considered speculative and is not intended to limit the disclosed process to any particular mechanism.

Nonionic, polar organic compounds containing a hydroxy group are of particular importance as the nonionic, polar organic material. Of note are nonionic, polar organic compounds which contain one or more hydroxy groups as the only functional group, or one or more hydroxy groups and one or more ether linkages as the only functional groups. Such hydroxy-containing compounds include monoalcohols, diols, polyols, glycols, polyglycols and various ether derivatives thereof.

Aliphatic, cycloaliphatic and araliphatic monoalcohols which form a second liquid phase in the reaction medium are suitable as the nonionic, polar organic material. For example $C_4$–$C_{10}$ aliphatic monoalcohols are suitable for use in the present process. However, the lower boiling aliphatic monoalcohols, with correspondingly low flashpoints, are not favored due to the additional safety precautions which are required. The higher boiling aliphatic monoalcohols are also not favored because they tend to become progressively less soluble and more difficult to remove from the quinacridone product of the oxidation. The araliphatic monoalcohols are those wherein a hydroxy functional group is present in an aliphatic side chain, preferably a $C_1$–$C_6$ side chain, for example benzyl alcohol.

Diols, polyols, glycols and polyglycols are particularly useful hydroxy containing compounds. Low molecular weight diols and triols, such as propylene glycol and glycerine, are too soluble in the reaction medium and do not form a second-phase. However, higher molecular weight diols, such as the $C_4$–$C_8$ diols, especially the $C_4$–$C_6$ diols, in particular 1,2-hexanediol and 1,6-hexanediol, are effective as the nonionic, polar organic material. Glycols, such as $C_6$–$C_8$-glycols, especially hexylene glycol (2-methyl-2,4-pentanediol), and di-, tri- or tetra-alkylene glycols having 6 to 12 carbon atoms, for example dipropylene glycol, tripropylene glycol or tetrapropylene glycol, are suitable along with the corresponding monoalkyl ether derivatives, especially mono-$C_1$–$C_6$ alkyl ether derivatives, for example dipropylene glycol monobutyl ether.

The polyglycols, such as alkylene oxide polymers, copolymers and block copolymers, for example polyethylene glycol or copolymers and block copolymers of ethylene oxide and propylene oxide, which have the required solubility properties, are suitable for use as the nonionic, polar organic material. Polyethylene glycols having a molecular weight in the range from about 200 to about 600, preferably about 400, are especially suitable as the nonionic, polar organic material. Ethylene diamine derivatives which are substituted by four alkylene oxide chains are also suitable for use in the present process.

Such compounds that are useful as the nonionic, polar organic material include, but are not limited to, 1-pentanol, 1-hexanol, 1- or 2-heptanol, 1- or 2-octanol, 1,2-pentanediol, 2-methyl-2,4-pentanediol, 1,2-hexanediol, 1,6-hexanediol, 1,2-heptanediol, 1,7-heptanediol, ethylene glycol monobutyl ether, dipropylene glycol, dipropylene glycol monomethyl ether, dipropylene glycol monobutyl ether, tripropylene glycol, tripropylene glycol monomethyl ether, benzyl alcohol, 2-phenyl-1-ethanol, polyethylene glycol having a molecular weight of about 400 and polyethylene glycol having a molecular weight of about 600.

In an embodiment of this invention, the second-phase forming organic material has a high boiling point, for example above about 200° C. Utilizing a high boiling material is advantageous because it eliminates the need for condensers and other equipment which is used to prevent atmospheric pollution through vaporization of the organic solvents. Suitable high-boiling, second-phase forming organic materials include various high-boiling polyglycols.

The present oxidation step is carded out in a highly basic, aqueous reaction medium. Alkali metal hydroxides, for example, sodium hydroxide and potassium hydroxide, are especially suitable as the base. Sodium hydroxide is particularly suitable.

In general, the base is present in at least an amount wherein the nonionic, polar organic material forms a second liquid phase in the reaction medium. In addition, the base serves the function of forming a salt form of the dihydroquinacridone in the aqueous medium. In general, the aqueous base in the reaction medium contains from 10 to 40, preferably 15 to 35, weight percent of the base, based on the weight of the aqueous base.

Preferably, the effective amount of the quinone compound is significantly less than the stoichiometric amount and the molecular oxygen is present as an oxygen-containing gas which is bubbled through the reaction medium or blown above the surface of the reaction medium.

As discussed above, the quinone compounds are described in the art as oxidizing agents and as catalysts. Suitable quinone compounds are, for example, anthraquinones, phenanthraquinones or napthaquinones, especially their sulfonic acid and carboxylic acid derivatives, or salts thereof. Anthraquinone and its derivatives such as mono- or di-chloroanthraquinone or the anthraquinone mono- or di-sulfonic acids, especially anthraquinone-2-sulfonic acid or anthraquinone-2,6-disulfonic acid and their derivatives, such as their salts, are particularly suitable. Anthraquinone-2-sulfonic acid and its salts are preferred quinone compounds.

The acid salts in the preceding paragraph are preferably alkali metal salts.

Generally, the quinone compound is an anthraquinone mono- or di-sulfonic acid, or a salt thereof, and the oxygen-containing gas comprises at least 2 percent by volume of molecular oxygen, the rest being a gas which is inert under the reaction conditions, for example, oxygen/nitrogen or oxygen/argon mixtures. In a specific embodiment of this invention, the oxygen-containing gas is air.

The quinone compound is present in an amount which is effective to oxidize the 6,13-dihydroquinacridone. In general, this is an amount ranging from 0.005 to 0.15 times, preferably 0.01 to 0.09 times, especially 0.01 to 0.02 times, the weight of 6,13-dihydroquinacridone or derivative.

It is preferred to carry out the oxidation at an elevated temperature, preferably above about 70° C., because the reaction does not proceed at a reasonable rate at lower temperatures. Thus, the oxidation is normally carried out at a temperature above 70° C., especially in the range from 90° C. to about 105° C. It is possible to carry out the oxidation at higher temperatures. However, such higher temperatures do not offer any advantage and may even prove troublesome.

Thus, a favored embodiment of the inventive process is a process which is carded out at an elevated temperature, wherein the nonionic, polar organic material is a monoalcohol, a diol, a glycol, a polyglycol or a mono-$C_1$–$C_6$ alkyl ether derivative of a diol, a glycol or a polyglycol, the base is an alkali metal hydroxide selected from the group consisting of sodium hydroxide and potassium hydroxide, the aqueous base in the reaction medium contains from 15 to 35 weight percent of the base, and the reaction medium contains from 7.5 to 10 parts by weight of the 6,13-dihydroquinacridone and from 0.5 to 1.2 parts by weight of the organic material per 100 parts of by weight of aqueous base in the reaction medium. An especially favored embodiment is the embodiment described above wherein the nonionic, polar organic material is 1-pentanol, 1-hexanol, 1or 2-heptanol, 1- or 2-octanol, 1,2-pentanediol, 2-methyl-2,4-pentanediol, 1,2-hexanediol, 1,6-hexanediol, 1,2-heptanediol, 1,7-heptanediol, ethylene glycol monobutyl ether, dipropylene glycol, dipropylene glycol monomethyl ether, dipropylene glycol monobutyl ether, tripropylene glycol, tripropylene glycol monomethyl ether, benzyl alcohol, 2-phenyl-1-ethanol, polyethylene glycol having a molecular weight of about 400 and polyethylene glycol having a molecular weight of about 600, in particular the process wherein the quinone compound is an anthraquinone-mono or di-sulfonic acid, or a salt thereof, which is present in less than the stoichiometric amount, especially anthraquinone-2-sulfonic acid, or a salt thereof, and the molecular oxygen is present as an oxygen containing gas which is bubbled through the medium or blown across the surface of the medium.

Although the reaction medium can consist of or consist essentially of only the aqueous base, the dihydroquinacridone, the quinone and molecular oxygen, the second-phase forming organic material and the optional particle growth inhibitor or crystal seed, it is possible for the reaction medium to further comprise minor amounts of other additives, including various surfactants, for example ionic surfactants, dispersants, peroxide scavengers, and phase transfer agents, without departing from the scope of this invention.

The presence of the second-phase forming organic material also improves known aqueous air oxidation processes, for example those disclosed in U.S. Pat. No. 3,738,988 and U.S. Pat. No. 5,093,497. Thus, the present process embraces those processes wherein the reaction medium additionally comprises a quaternary ammonium compound and/or a divalent iron, cobalt or nickel cation.

The unsubstituted and substituted 6,13-dihydroquinacridones oxidized in the present process are also well-known in the art and can be prepared, for example, from 2,5-diarylamino-3,6-dihydroterephthalic esters by processes known in the art.

The quinacridone compounds prepared by the present process are well-known as pigments. In general, the quinacridone pigments correspond to compounds of the formula

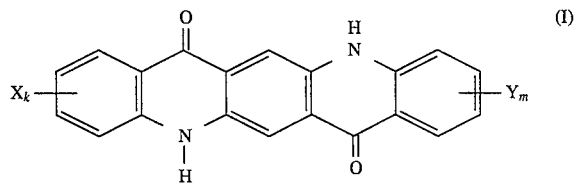

wherein X and Y are independently H, halogen, in particular F or Cl, carboxyl, $C_1$–$C_4$alkyl, trifluoromethyl or $C_1$–$C_4$alkoxy and k and m are integers from 0 to 2. Of particular significance as pigments are the unsubstituted (wherein X and Y are H) and 4,11- and 2,9-disubstituted quinacridones, especially 4, 11- and 2,9-dichloroquinacridone, 4,11- and 2,9-dimethylquinacridone, and 2,9-difluoroquinacridone. All of these quinacridone pigments are prepared according to the present process.

The disclosed process is especially suitable for the preparation for unsubstituted quinacridone pigments. The unsubstituted quinacridone pigments are known to exist in alpha, beta and gamma crystal modifications. When prepared according to the present process, the crystal phase of the unsubstituted quinacridone product is influenced by a number of factors, including the presence or absence of particle growth inhibitors and/or seed crystals, the base concentration and the identity of the nonionic, polar organic material. Since the thermodynamic energy differences among the crystal phases are small, the phase direction is influenced by relatively minor reaction medium changes. Thus, it is not always possible to predict the crystal phase of the unsubstituted quinacridone product.

The beta phase is favored by higher base concentrations and the presence of certain impurities, particle growth inhibitors and/or β-seed crystals. Thus, a beta quinacridone is normally prepared if an alpha- or beta- dihydroquinacridone is oxidized under the present reaction conditions in the presence of a beta crystal seed or a particle growth inhibitor. Such particle growth inhibitors are well-known in the an and are generally sulfonic acid, phthalimidomethyl-, imidazolylmethyl-, pyrazolylmethyl- or N-(dialkylaminoalkyl)sulfonic acid amide derivatives of quinacridone, especially phthalimidomethylquinacridone or quinacridone sulfonic acid, aluminum salt. In addition, higher base concentrations, such as from 25 to 35 weight-percent of the base, especially about 30 weight-percent, based on the weight of the aqueous base in the reaction medium, favors formation of the [3-crystal phase of the unsubstituted quinacridone.

Of note is a process wherein the 6,13-dihydroquinacridone is unsubstituted alpha- or beta-phase 6,13-dihydroquinacridone, the quinacridone is unsubstituted beta-phase quinacfidone and the medium additionally comprises a beta-phase quinacfidone crystal seed or a particle growth inhibitor, especially those wherein the quinone compound is anthraquinone-2-sulfonic acid, the base is sodium hydroxide and the aqueous base in the reaction medium contains about 30 weight percent of the base, in particular, such a process wherein the nonionic, polar organic material is polyethylene glycol having a molecular weight of about 400 or 1,2-hexane diol.

Generally, the alpha or gamma crystal forms are favored in the absence of particle growth inhibitors and β-seed crystals, especially at lower base concentrations, for example from 10 to about 25 weight-percent of the base, based on the weight of aqueous base in the reaction medium.

After the oxidation step described above is complete, the quinacridone product is isolated by customary methods known to those skilled in the art, for example, by filtering, washing with water until colorless and/or free of base and then drying.

The quinacridones produced by the present process are used directly as pigments or are further processed, such as by a conventional particle-size reducing step, to produce the desired pigment. Such further processing steps are familiar to one skilled in the art.

The following examples further describe but do not limit the scope of the present invention.

EXAMPLE 1

The following ingredients are added to a one liter laboratory blender: 60 g water, 300 g 50% sodium hydroxide, 40 g 2,9-dichloro-6,13-dihydroquinacridone, 5.0 g of polyethylene glycol (M.W. 400), abbreviated PEG-400, and 0.80 g anthraquinone-2-sulfonate, sodium salt. After mixing, the contents are transferred to a 1l flask fitted with stirrer, thermometer and condenser. Air is admitted at a rate of 1 liter/min during heat up to 105° C. and throughout the remaining hold period of five hours. The resultant product is filtered, washed and dried. XRD analysis shows a mixture of alpha and gamma 2,9-dichloroquinacridone with a spectrophotometrically determined 93% quinacridone assay.

EXAMPLE 2

The following ingredients are added to a one liter laboratory blender: 200 g water, 240 g 50% sodium hydroxide, 40 g alpha-phase, 6,13-dihydroquinacridone, and 2.5 grams of PEG-400. After mixing, the contents are transferred to a 1l flask fitter with stirrer, thermometer and condenser. The contents are heated to 90° C. and held for one hour. Then, 1.60 g anthraquinone-2-sulfonate, sodium salt is added and air is admitted at a rate of 1 liter/min during heat up to 105° C. and throughout the remaining hold period of five hours. The resultant product is filtered, washed and dried. XRD analysis shows the product to be essentially gamma quinacridone with a spectrophotometrically determined, 80% quinacridone assay.

EXAMPLE 3

The procedure of Example 2 is repeated except for the inclusion of 0.20 g phthalimidomethylquinacridone during the oxidation phase. XRD analysis shows the product to be beta quinacridone with 92.9% quinacridone assay.

EXAMPLE 4

The following ingredients are added to a one liter laboratory blender: 200 g water, 240 g 50% sodium hydroxide, 40 g alpha phase 6,13-dihydroquinacridone, 4.0 g dipropylene glycol monobutyl ether, and 0.80 g anthraquinone-2-sulfonate, sodium salt. After mixing, the contents are transferred to a 1l flask fitted with stirrer, thermometer and condenser. Air is admitted at a rate of 1 liter/min during heat up to 100 ° C. and throughout the remaining hold period of five hours. The resultant product is filtered, washed and dried. XRD analysis shows alpha quinacridone with a spectrophotometrically determined, 91.5% quinacridone assay. The product has an attractive red masstone.

EXAMPLE 5

The following ingredients are added to a one liter laboratory blender: 180 g water, 270 g 50% sodium hydroxide, 44 g alpha phase 6,13-dihydroquinacridone, 3.3 g PEG-400, 0.80 g anthraquinone-2-sulfonate, sodium salt and 0.60 g crude beta quinacridone "seed". After mixing, the contents are transferred to a 1l flask fitter with stirrer, thermometer and condenser. Air is admitted at a rate of 1 liter/min during heat up to 100° C. and throughout the remaining hold period of four hours. The resultant product is filtered, washed and dried. XRD analysis shows beta quinacridone with a spectrophotometrically determined 95.5% quinacridone assay. The product has an opaque masstone or is particle size reduced to a conventional violet pigment.

EXAMPLE 6

The following ingredients are added to a one liter laboratory blender: 180 g water, 270 g 50% sodium hydroxide, 40 g alpha phase 6,13-dihydroquinacridone, 3.0 g PEG-400, 0.80 g anthraquinone-2-sulfonate, sodium salt and 2.0 g of a 10% slurry of quinacridone monosulfonate, aluminum salt. After mixing, the contents are transferred to a 1l flask fitted with stirrer, thermometer and condenser. Air is admitted at a rate of 1 liter/min during heat up to 100° C. and throughout the remaining hold period of four hours. The resultant product is filtered, washed and dried. XRD analysis shows beta quinacridone with a spectrophotometrically determined 94.4% quinacridone assay.

EXAMPLE 7

The following ingredients are added to a one liter laboratory blender: 180 g water, 270 g 50% sodium hydroxide, 40 g alpha phase 6,13-dihydroquinacridone, 4.0 g 1,2-hexanediol, 0.80 g anthraquinone-2-sulfonate, sodium salt and 1.0 g of crude beta quinacridone "seed". After mixing, the contents are transferred to a 1l flask fitted with stirrer, thermometer and condenser. Air is admitted at a rate of 1 liter/min during heat up to 90° C. and throughout the remaining hold period of four hours. The resultant product is filtered, washed and dried. XRD analysis shows beta quinacridone with a spectrophotometrically determined 97.6% quinacridone assay.

EXAMPLE 8

The following ingredients are added to a one liter laboratory blender: 180 g water, 270 g 50% sodium hydroxide, 40 g beta phase 6,13-dihydroquinacridone, 4.0 g PEG-400, and 0.80 g anthraquinone-2-sulfonate, sodium salt. After mixing, the contents are transferred to a 1l flask fitted with stirrer, thermometer and condenser. Air is admitted at a rate of 1 liter/min during heat up to 90° C. and throughout the remaining hold period of five hours. The resultant product is filtered, washed and dried. XRD analysis shows gamma quinacridone with a spectrophotometrically determined 95% quinacridone assay.

In addition to the embodiments described above, numerous variations of these embodiments can be made in accordance with this invention.

I claim:

1. A process for preparing an unsubstituted or substituted quinacridone, which process comprises an oxidation step wherein a 6,13-dihydroquinacridone is converted to the corresponding quinacridone in a basic, aqueous reaction medium utilizing a quinone compound and molecular oxygen as oxidizing agent, which reaction medium consists essentially of 100 parts by weight of an aqueous base, from 6 to 12 parts by weight of the 6,13-dihydroquinacridone, from 0.5 to 3 parts by weight of a nonionic, polar organic material which forms a second liquid phase in the basic reaction medium and which is an aliphatic monoalcohol, a cycloaliphatic monoalcohol, an araliphatic monoalcohol, a $C_4$–$C_8$diol, $C_6$–$C_8$glycol, polyglycol or a mono-$C_1$–$C_6$alkyl ether derivative of a $C_4$–$C_8$diol, $C_6$–$C_8$glycol or a polyglycol, and an effective oxidizing amount of the quinone compound and molecular oxygen.

2. A process of claim 1 wherein the reaction medium comprises from 7.5 to 10 parts by weight of the 6,13-dihydroquinacridone.

3. A process of claim 2 wherein reaction medium comprises from 0.5 to 1.2 parts by weight of the organic material.

4. A process of claim 1 wherein the organic material is a polyglycol.

5. A process of claim 1 wherein the organic material is a $C_4$–$C_8$diol, a $C_6$–$C_8$glycol, a polyglycol or a mono-$C_1$–$C_6$alkyl ether derivative of a $C_4$–$C_8$diol, a $C_6$–$C_8$glycol or a polyglycol.

6. A process of claim 1 wherein the organic material is 1-pentanol, 1-hexanol, 1- or 2-heptanol, 1-or 2-octanol, 1,2-pentanediol, 2-methyl-2,4-pentanediol, 1,2-hexanediol, 1,6-hexanediol, 1,2-heptanediol, 1,7-heptanediol, dipropylene glycol, dipropylene glycol monomethyl ether, dipropylene glycol monobutyl ether, tripropylene glycol, tripropylene glycol monomethyl ether, benzyl alcohol, 2-phenyl-1-ethanol, diethanolamine, triethanolamine, polyethylene glycol having a molecular weight of about 400 and polyethylene glycol having a molecular weight of about 600.

7. A process of claim 6 wherein the organic material is 1,2-hexanediol or polyethylene glycol having a molecular weight of about 400.

8. A process of claim 1 wherein the organic material has a boiling point above 200° C.

9. A process of claim 1 wherein the base is an alkali metal hydroxide.

10. A process of claim 9 wherein the base is selected from the group consisting of potassium hydroxide and sodium hydroxide.

11. A process of claim 9 wherein the aqueous base in the reaction medium contains from 10 to 40 weight percent of the base.

12. A process of claim 9 wherein the aqueous base in the reaction medium contains from 15 to 35 weight percent of the base.

13. A process of claim 1 wherein the quinone compound is present in less than the stoichiometric amount and the molecular oxygen is present as an oxygen-containing gas which is bubbled through the medium or blown above the surface of the medium.

14. A process of claim 13 wherein the quinone compound is an anthraquinone mono- or di-sulfonic acid, or a salt thereof, and the oxygen-containing gas comprises at least 2 percent by volume of molecular oxygen.

15. A process of claim 13 wherein the oxygen-containing gas is air.

16. A process of claim 13 wherein the oxidation is carried out at a temperature in the range from 90° C. to 105° C.

17. A process of claim 12 wherein the quinacridone has the formula

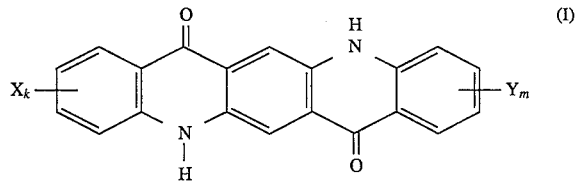

wherein X and Y are independently H, F, Cl, carboxyl, $C_1$–$C_4$alkyl, trifluoromethyl or $C_1$–$C_4$alkoxy and k and m are integers from 0 to 2.

18. A process of claim 17 wherein the quinacridone is unsubstituted quinacridone.

19. A process of claim 13 wherein the 6,13-dihydroquinacridone is unsubstituted alpha- or beta-phase 6,13-dihydroquinacridone, the quinacridone is unsubstituted beta-phase quinacridone and the medium additionally comprises a beta-phase quinacridone crystal seed or a particle growth inhibitor.

20. A process of claim 19 wherein the particle growth inhibitor is selected from the group consisting of phthalimidomethylquinacridone and quinacridone sulfonic acid, aluminum salt.

21. A process of claim 19 wherein the base is an alkali metal hydroxide is which selected from the group consisting of sodium hydroxide and potassium hydroxide and the aqueous base in the reaction medium contains from 25 to 35 weight percent of the base.

22. A process of claim 21 wherein the organic material is a polyglycol.

23. A process of claim 21 wherein the quinone compound is anthraquinone-2-sulfonic acid, or a salt thereof, the base is sodium hydroxide and the aqueous base in the reaction medium contains about 30 weight percent of the base.

24. A process of claim 21 wherein the organic material is polyethylene glycol having a molecular weight of about 400 or 1,2-hexane diol.

25. A process of claim 24 wherein the organic material is polyethylene glycol having a molecular weight of about 400.

26. A process of claim 3 wherein the organic material is 1-pentanol, 1-hexanol, 1- or 2-heptanol, 1- or 2-octanol, 1,2-pentanediol, 2-methyl-2,4-pentanediol, 1,2-hexanediol, 1,6-hexanediol, 1,2-heptanediol, 1,7-heptanediol, ethylene glycol monobutyl ether, dipropylene glycol, dipropylene glycol monomethyl ether, dipropylene glycol monobutyl ether, tripropylene glycol, tripropylene glycol monomethyl ether, benzyl alcohol, 2-phenyl-1-ethanol, polyethylene glycol having a molecular weight of about 400 and polyethylene glycol having a molecular weight of about 600.

27. A process of claim 26 wherein the quinone compound is anthraquinone-2-sulfonic acid, or a salt thereof.

* * * * *